(12) United States Patent
Oh et al.

(10) Patent No.: US 6,506,919 B1
(45) Date of Patent: Jan. 14, 2003

(54) METALLOCENE COMPOUNDS AND THEIR USE FOR OLEFIN POLYMERIZATION

(75) Inventors: Jae-Seung Oh, Taejeon (KR); Bun-Yeoul Lee, Taejeon (KR); Joo-Eun Lee, Taejeon (KR); Do-Hoon Lee, Kyungki-do (KR)

(73) Assignee: LG Chemical Co., Ltd., Seoul (KR)

( * ) Notice: Subject to any disclaimer, the term of this patent is extended or adjusted under 35 U.S.C. 154(b) by 0 days.

(21) Appl. No.: 09/914,717

(22) PCT Filed: Mar. 3, 2000

(86) PCT No.: PCT/KR00/00167
§ 371 (c)(1),
(2), (4) Date: Aug. 31, 2001

(87) PCT Pub. No.: WO00/52063
PCT Pub. Date: Sep. 8, 2000

(30) Foreign Application Priority Data

Mar. 3, 1999 (KR) ............................................... 99-6955
Mar. 2, 2000 (KR) ............................................... 00-10348

(51) Int. Cl.$^7$ .......................... C07F 17/00; B01J 31/00; C08F 4/642
(52) U.S. Cl. .......................... 556/11; 556/53; 526/126; 526/160; 526/161; 526/352; 526/943; 502/103; 502/117; 502/120
(58) Field of Search ..................... 556/11, 53; 502/103, 502/117, 120; 526/126, 160, 161, 352, 943

(56) References Cited

U.S. PATENT DOCUMENTS 5,312,938 A * 5/1994 Hefner et al. ................. 556/11
6,355,819 B1 * 3/2002 Leino et al. .................. 556/11

FOREIGN PATENT DOCUMENTS

| EP | 372414 A2 | * | 6/1990 |
| EP | 662484 A2 | * | 7/1995 |
| EP | 0839836 A1 | * | 5/1998 |
| WO | WO 94/28034 A1 | * | 12/1994 |
| WO | WO 97/28170 A1 | * | 8/1997 |

* cited by examiner

Primary Examiner—Porfirio Nazario-Gonzalez
(74) Attorney, Agent, or Firm—Ladas & Parry

(57) ABSTRACT

The present invention relates to a metallocene compound and the olefin polymerization using the same, particularly to a metallocene compound and the olefin polymerization using this compound on which supported catalysts are easily prepared by the reaction of the ligand containing —$(CR^1_2)_a$—O—$SiR_bY_c$ ligand (wherein each Y, which can be the same as or different from other Y, is a hydrogen, halogen, alkoxy, aryloxy, amide, or silyloxy radical, each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms, each R, which can be the same as or different from other R, is an alkyl, cycloalkyl, aryl, alkenyl, alkylaryl, arylalkyl, or arylalkenyl radical having from 1 to 40 carbon atoms, a is an integral number from 1 to 40, c is 1, 2, or 3, and the sum of b and c is 3) with a support. Furthermore, the present invention relates to a supported metallocene catalyst using this metallocene compound and the olefin polymerization using the same. The metallocene compounds in this invention have superior characteristics in the preparation of supported catalyst due to the high reactivity with the support and minimal side reactions during the anchoring process. In addition, the olefin polymerization process employing the supported catalyst in this invention proceeds without fouling in the reactor, and the morphology and bulk density of the polymer produced are better than that produced by the conventional method.

12 Claims, No Drawings

METALLOCENE COMPOUNDS AND THEIR USE FOR OLEFIN POLYMERIZATION

BACKGROUND OF THE INVENTION (a) Field of the Invention

The present invention relates to a metallocene compound and the olefin polymerization using the same, particularly to a metallocene containing $-CR^1{}_2)_a-O-SiR_bY_c$ ligand as a part of a ligand, so that the preparation of a supported metallocene catalyst is convenient (wherein each Y, which can be the same as or different from other Y, is a hydrogen, halogen, alkoxy, aryloxy, or amide radical; each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms; each R, which can be the same as or different from other R, is an alkyl, cycloalkyl, aryl, alkenyl, alkylaryl, arylalkyl, or arylalkenyl radical having from 1 to 40 carbon atoms, a is an integral number of from 1 to 40, c is 1, 2, or 3, and the sum of b and c is 3). Furthermore, the present invention relates to a supported metallocene catalyst using this metallocene compound and the olefin polymerization using the same.

The metallocene compound in this invention has superior reactivity with support in the preparation of supported metallocene catalyst, so that side reactions can be minimized and the olefin polymerization activity using the catalyst in this invention is excellent. In addition, the olefin polymerization process employing the supported metallocene catalyst of this invention shows no fouling in a reactor and produces polymer with well defined particle size and bulk density.

(b) Description of the Related Art

In 1976, Professor Kaminsky of Germany reported that olefin polymerization could be accomplished using zirconocenedichloride compound as a catalyst with methylaluminoxane (MAO) as a co-catalyst which was obtained through the partial hydrolysis of trimethylaluminum (A. Anderson, J. G. Corde. J. Herwig, W. Kaminsky, A. Merck, R. Mottweiler, J. Pein, H. Sinn, and H, J. Vollmer, Angew. Chem. Int. Ed. Engl. 15, 630, (1976)).

Thereafter, Exxon filed a patent (U.S. Pat. No. 5,324,800) on the olefin polymerization utilizing the metallocene compounds with various substituent groups.

This homogeneous olefin polymerization catalyst shows unique polymerization characteristics which can not be observed by conventional Ziegler-Natta catalysts. That is, the molecular weight distribution of produced polymers is narrow, co-polymerization is easy, and the distribution of the comonomer is uniform. In the case of the propylene polymerization, the tacticity of polymer can be controlled according to the molecular symmetry of catalyst. These unique characteristics not only opened up a way to new polymers which are not obtained by the conventional Ziegler-Natta catalyst, but also provided the way to tailor-made polymers. Accordingly, there have been continuous interests on this catalyst system.

In a gas phase or in a slurry process, the particle morphology and bulk density of a produced polymer should be controlled to enhance the easy transfer of polymer and to increase the throughput per reactor unit volume. Also, the reactor fouling should be avoided for a continuous operation. To solve these problems, the catalyst should be supported on a suitable support.

Described below are conventional preparation methods for supported metallocene catalysts.

In first, a metallocene compound is physisorbed on a support, and then supported by treatment with aluminoxane (W. Kaminsky, Makromol. Chem., Rapid Commun. 14, 239 (1993)).

Secondly, aluminoxane is supported on a support, and then a metallocene compound is supported (K. Soga, Makromol. Chem. Rapid Commun. 13, 221 (1992); U.S. Pat. No. 5,006,500; U.S. Pat. No. 5,086,025).

Thirdly, a metallocene compound is treated with aluminoxane, and then supported on a support (U.S. Pat. No. 5,240,894).

Additionally, anchoring is achieved by a chemical reaction between the ligand of a metallocene compound and a support. In one case, metal is ligated after ligand is supported. (K. Soga, H. J. Kim, T. Shiono, Makromol., Rapid Commun. 15, 139 (1994), Japanese Laid-open Patent No. Heisei 6-56928; U.S. Pat. No. 5,466,766).

In the other case, a metallocene compound with a reactive functional group on a ligand is prepared and then it is anchored by a chemical reaction between the functional group on a ligand and a support. In all cases, the catalyst must be strongly supported on a support surface by a chemical bond. Supported metallocene catalyst obtained by contacting metallocene compound without a reactive ligand with a support such as silica results in reactor fouling due to the leaching of metallocene compound.

The following Reaction Formulae 1 to 5 list chemical reactions which are possible on the support surface:

[Reaction Formula 1]

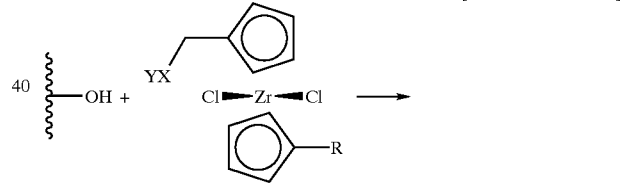

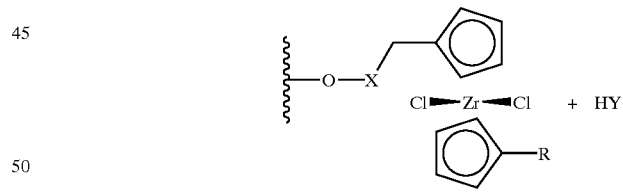

[Reaction Formula 2]

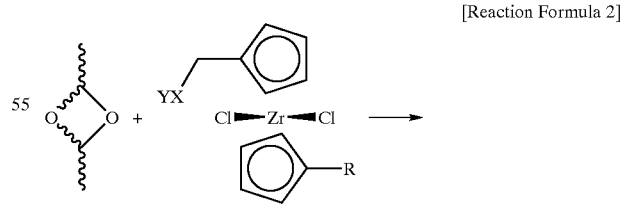

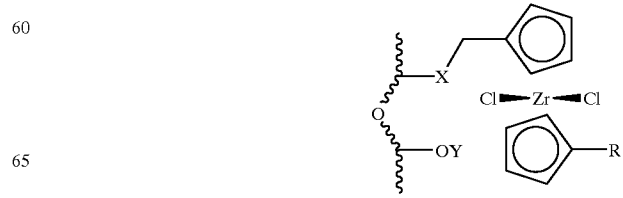

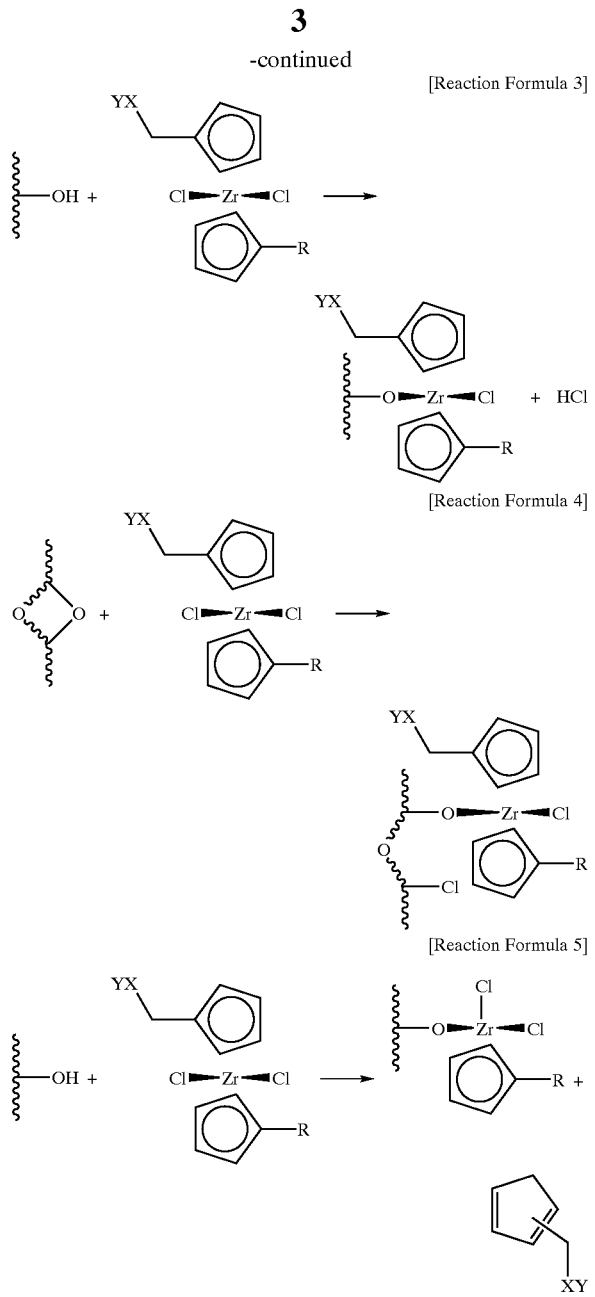

The above Reaction Formula 1 and Reaction Formula 2 show desirable supporting reactions resulting from the interaction between the functional group of a ligand and the hydroxyl group or reactive oxo functional group on the support surface. The Reaction Formulae 3 to 5 show side reactions.

Additionally, various side reactions involving functional groups on the support surface result in decomposition of the metallocene compounds. Also weakly physisorbed metallocene compounds can be found on the support.

The anchoring of the colorless metallocene compounds on the colorless silica support usually yields brown or dark gray colored supported metallocene compounds. This color change indicates accompanied side reactions described above during the supporting process.

The supported metallocene compounds produced by the side reactions are not activated by co-catalysts and show decreased catalyst activity. The catalyst made by the side reactions, even if activated, will dissolve into a solvent and cause undesirable problems such as reactor fouling or reduced bulk density of the polymer.

These problems due to the side reactions can be overcome by a soxhlet method by which the weakly physisorbed metallocene compounds or decomposed by-products are extracted from the support surface before polymerization process.

More basically, the development of metallocene compounds with suitable ligands which can react with functional groups on the support surface is a solution for this problem. With appropriate ligand systems, reactions described in Reaction Formulae 1 and 2 are maximized, and a supported catalyst can be obtained in a high yield.

Previously reported metallocene compounds with suitable functional groups that can react with support are summarized as follows.

European Patent No. 293,815 A1 discloses a method in which a supported metallocene catalyst is prepared by the reaction of a metallocene compound containing —C—SiR$_2$(OR') functional group (wherein R is a $C_1$–$C_4$ alkyl, $C_6$–$C_{10}$ aryl, or $C_1$–$C_4$ alkoxy, and OR' is a $C_1$–$C_4$ alkoxy) with a support containing a hydroxyl group on its surface. Olefin polymerization utilizing this supported catalyst activated by an aluminoxane was presented.

Supported metallocene compounds can be prepared by the reaction of metallocene compound containing an alkoxysilyl functional group similar to that described above with a support containing highly reactive siloxane functionality as presented by these inventors (Korean Patent No. 98-12660).

U.S. Pat. No. 5,767,300 discloses a metallocene compound with —C—$ZR_oHal_p$ (Z is boron, silicon, germanium or tin; each $R_o$, which can be the same as or different from other $R_o$, is a hydrogen radical or a hydrocarbyl radical having from 1 to 20 carbon atoms; Hal is halogen radical; o is 0, 1, or 2; p is 1, 2 or 3) ligand functional group, preparation of supported metallocene compound, and olefin polymerization process using the supported catalyst.

Additionally, the preparation of a metallocene compound containing at least one —OSiR$_3$ (R is $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl radical.) functional group, preparation of supported metallocene compound, and olefin polymerization process using the supported catalyst are disclosed in European Patent No. 839,836 A1.

These catalysts can be used for the olefin polymerization catalyst after activated by a suitable co-catalyst. However, employing a supported metallocene catalyst prepared by the anchoring of a metallocene catalyst on a suitable support is more favorable for olefin polymerization. Therefore, the development of metallocene catalyst which contains a reactive functional group and is available to anchoring on a support is required to minimize various side reactions during the supporting process.

The development of the catalyst with a reactive functional group leads to a highly active supported catalyst which can provide polymers with superior morphology and bulk density and minimize the fouling of the reactor, so that the catalysts can be employed in the existing process.

SUMMARY OF THE INVENTION

It is an object of the present invention to provide a metallocene compound that has an excellent reactivity with a support to produce supported catalyst.

It is another object of the present invention to provide an olefin polymerization method using the above metallocene compound.

It is still another object of the present invention to provide a supported metallocene catalyst in which the above metallocene compound is chemically bound to a support.

It is still another object of the present invention to provide an olefin polymerization method using the above supported metallocene catalyst.

DETAILED DESCRIPTION OF THE PREFERRED EMBODIMENTS

In the following detailed description, only the preferred embodiment of the invention has been shown and described, simply by way of illustration of the best mode contemplated by the inventors of carrying out the invention. As will be realized, the invention is capable of modification in various obvious respects, all without departing from the invention. Accordingly, descriptions are to be regarded as illustrative in nature, and not restrictive.

In order to achieve the above objects, the present invention provides a metallocene catalyst component for the olefin polymerization which facilitates the preparation of the supported metallocene catalyst and is represented by the following Chemical Formulae 1 or 2 in which at least one of the hydrogen radicals of $R^2$, $R^3$ or B is substituted by a radical selected from the group represented by the Chemical Formula 3:

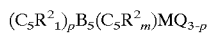 [Chemical Formula 1]

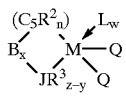 [Chemical Formula 2]

(wherein M is a transition metal of Group 4;

$(C_5R^2{}_l)$, $(C_5R^2{}_m)$ and $(C_5R_n{}^2)$ are a cyclopentadienyl ligand, a substituted cyclopentadienyl ligand, a substituted cyclopentadienyl ligand in which two adjacent carbon atoms of a $C_5$ are joined together to form one or more $C_4$–$C_{16}$ rings by a hydrocarbyl radical, in which each $R^2$, which can be the same as or different from other $R^2$, is a hydrogen radical, or an alkyl, cycloalkyl, aryl, alkenyl, alkylaryl, arylalkyl, or arylalkenyl radical having from 1 to 40 carbon atoms, or a metalloid of Group 14 substituted with hydrocarbyl radical;

B is an alkylene carbon chain, arylene carbon chain, alkenylene carbon chain, dialkyl germanium, dialkyl silicon, alkyl phospine or alkyl amine radical substituting on and bridging two cyclopentadienyl ligands, or a cyclopentadienyl ligand and $JR^3{}_{z-y}$ ligands by a covalent bond;

$R^3$ is a hydrogen radical, or an alkyl, alkenyl, aryl, alkylaryl, or arylalkyl radical having from 1 to 40 carbon atoms;

J is an element of Group 15 or 16;

each Q, which can be the same as or different from other Q, is a halogen radical, an alkyl, alkenyl, aryl, alkylaryl, or arylalkyl radical having from 1 to 20 carbon atoms, or an alkylidene radical having from 1 to 20 carbon atoms;

L is a Lewis base;

s is 0 or 1, p is 0, 1, or 2; (provided that p is 0 then s is 0; when s is 1 then l and m is 4; and when s is 0 then l and m is 5), and z is a valence number of J;

provided that J is an atom of Group 15, then z is 3; and when J is an atom of Group 16, then z is 2;

x is 0 or 1;

provided that x is 0, then n is 5, y is 1, and w is greater than 0; when x is 1, then n is 4, y is 2, and w is 0),

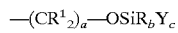 [Chemical Formula 3]

(wherein each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms, each R, which can be the same as or different from other R, is an alkyl, cycloalkyl, aryl, alkenyl, alkylaryl, arylalkyl, or arylalkenyl radical having from 1 to 40 carbon atoms, each Y, which can be the same as or different from other Y, is a hydrogen, halogen, alkoxy, aryloxy, or amide radical, a is an integral number from 1 to 40, c is 1, 2, or 3, and the sum of b and c is 3).

Additionally, in the polymerization process employing one or more olefin compounds, this invention provides a polymerization process comprising a) a metallocene catalyst compound in which at least one of the hydrogen radical of the $R^2$, $R^3$ or B of the Chemical Formulae 1 or 2 is substituted with a functional group represented by Chemical Formula 3; and b) a co-catalyst(s) selected from the compounds represented by the Chemical Formulae 4, 5, or 6 shown below:

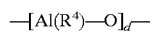 [Chemical Formula 4]

(wherein each $R^4$, which can be the same as or different from other $R^4$, is a halogen, or a hydrocarbyl or a halogen substituted hydrocarbyl radical having from 1 to 40 carbon atoms, and d is an integral number greater than 2).

 [Chemical Formula 5]

(wherein each $R^5$, which can be the same as or different from other $R^5$, is a halogen, or a hydrocarbyl or a halogen substituted hydrocarbyl radical having from 1 to 40 carbon atoms), and

 [Chemical Formula 6]

(wherein, $[L]^+$ is a cation composed of inorganic or organic group, $N^1$ is an element of Group 13, each E, which can be the same as or different from other E, is an aryl radical having from 6 to 40 carbon atoms, where more than one hydrogen radical of the aryl group is substituted with halogen radical, hydrocarbyl radical containing 1 to 40 carbons, alkoxy radical, phenoxy radical, or hydrocarbyl radical having from 1 to 40 carbon atoms containing nitrogen, phosphorus, sulfur or oxygen atom).

Furthermore, this present invention provides a supported metallocene catalyst prepared by the treatment of a) a metallocene catalyst compound in which at least one of the hydrogen radical of the $R^2$, $R^3$ or B of the Chemical Formulae 1 or 2 is substituted with a functional group represented by the Chemical Formula 3; and b) an inorganic support to yield a supported metallocene compound in which the metallocene compound of Chemical Formula a) is supported on an inorganic support of b).

Furthermore, in the polymerization process employing one or more olefin monomers, this invention provides a polymerization process comprising a) the treatment of i) a metallocene catalyst compound in which at least one of the hydrogen radical of the $R^2$, $R^3$ or B of the Chemical Formulae 1 or 2 is substituted with a functional group represented by the Chemical Formula 3; with ii) an inorganic support to yield a supported metallocene compound in which the metallocene compound of i) is supported on an inorganic support of ii), and b) a co-catalyst(s) selected from the compounds represented by the Chemical Formulae 4, 5, or 6 shown above.

Olefin polymerization process employing a mixed co-catalyst represented by the Chemical Formula 4 and 5 is recommended.

It is desirable to select one or more inorganic supports from a group comprised of silica, alumina, aluminum silicate. More specifically, the desirable inorganic support is a porous containing reactive surface hydroxyl group or oxo group resulting from a drying of the oxide support above 500° C. Especially, dehydrated silica or silica containing highly reactive surface siloxane group due to the thermal treatment above 500° C. is preferable.

The metallocene compound in this invention is fundamentally different from those described in the previous techniques.

For example, for the catalyst claimed in European Patent No. 293,815 A1, the —Si(OR') functional group is connected to the cyclopentadienyl ligand via a hydrocarbyl diradical or a hydrocarbyl diradical containing a silyl group. Also, the patent disclosed that the siloxane group should be substituted with a suitable functional group before the transition metal is ligated by ligands. Furthermore, the catalyst is anchored on a support weakly that excess amount of metallocene catalyst component is required to prepare the supported catalyst.

For the catalyst claimed in the U.S. Pat. No. 5,767,300, —SiR³₀Halₚ functional group is bonded to the cyclopentadienyl group through a bidentate group having 1 to 40 carbons.

In the catalyst disclosed in European Patent No. 839,836 A1, the —OSiR₃ group is limited to R of $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl radical. Compared to that, this invention presents a metallocene compound with —OSiR$_b$Y$_c$ functional group in which Y is a reactive functional group such as a hydrogen radical, a halogen radical, or an alkoxy radical. Due to the presence of two reactive functional groups, —OSiR$_b$Y$_c$ and Y in this metallocene compound, this invention is more reactive toward the support surface than conventional metallocene compounds. Comparative Example 1 shows the difference in the interaction between the support and the catalysts in this invention and [Me₃SiO—(CH₂)₆—C₅H₄]₂ZrCl₂ which is disclosed in European Patent 839,836 A1.

The functional group Y attached to a silicon atom affects the electronic and steric environment of the silicon atom, so that it facilitates the anchoring of the metallocene onto a support and reduces side reactions during the anchoring process.

Therefore, the soxhlet procedure, which is required to wash out the weakly physisorbed metallocene complexes on the support, can be avoided. Also the minimized side reactions, and the maximized supporting of the catalyst increase the efficiency of the metallocene catalyst for the polymerization reactions.

The present invention is illustrated by the following practical exercises in detail. However, the range of the present invention is not limited by these practical exercises

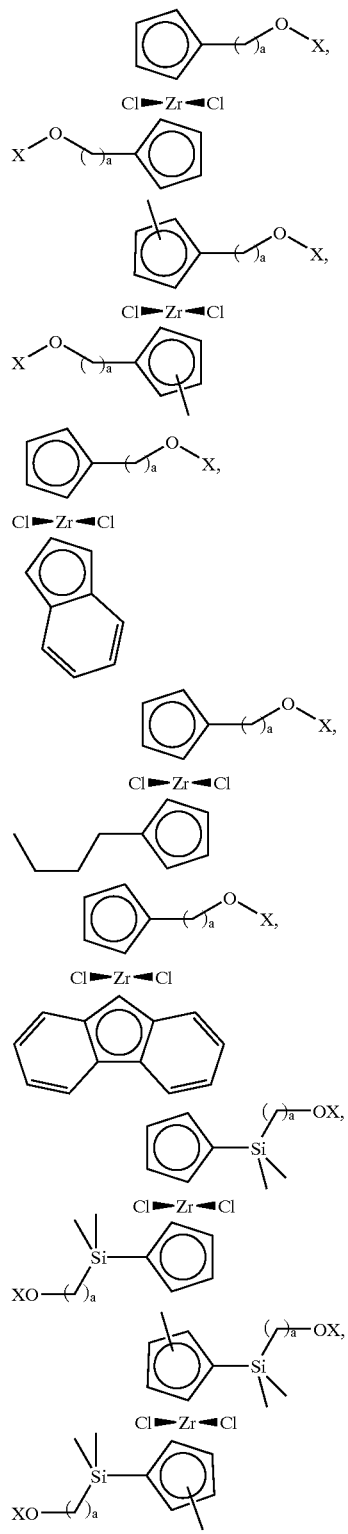

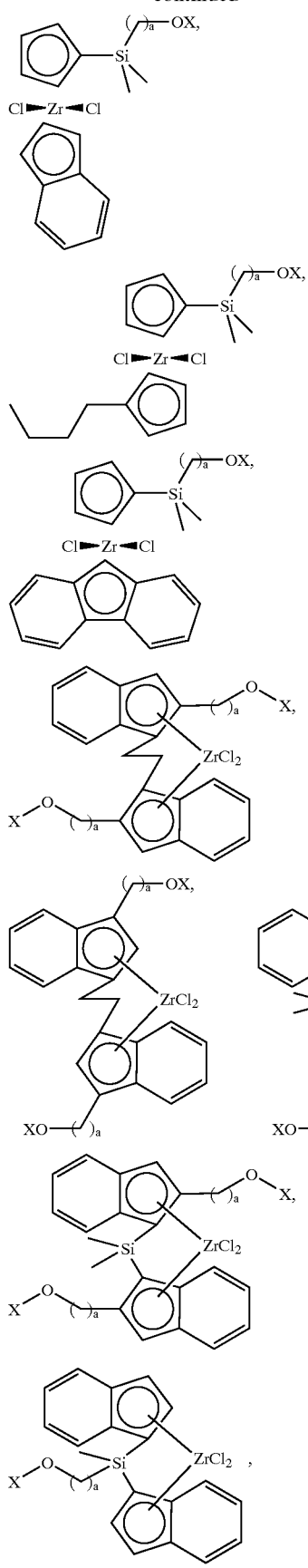
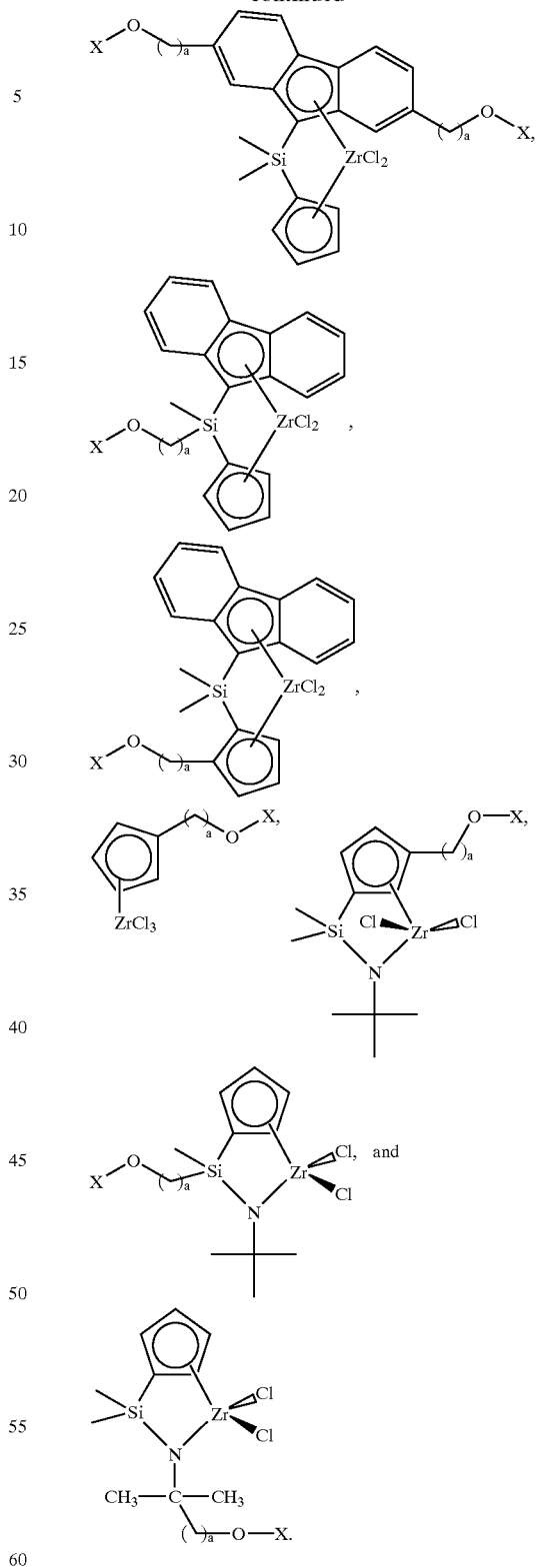
wherein, X can be $SiMe_2Cl$, $SiMeCl_2$, $SiCl_3$, $SiMe_2(OMe)$, $SiMe(OMe)_2$, $SiMe_2H$, $SiMeH_2$, $SiHMeCl$, $SiMe(OMe)_2$, $Si(OMe)_3$, $SiMe_2(OEt)$, $SiMe(OEt)_2$, $Si(OEt)_3$, $SiMe_2(NMe_2)$, $SiMe(NMe_1)_2$, $Si(NMe_2)_3$, $SiMe_2(NEt_2)$, $SiMe(NEt_2)_2$, $Si(NEt_2)_3$, etc.
Furthermore, a is an integer from 1 to 40, which determines the distance of the metallocene catalyst from the support surface. The oxygen atom of the siloxane group on the support surface may coordinate to the activated cationic catalyst and lead to a deactivation of the catalyst. However, if a is between 5 and 10, the coordination of the activated cation and oxygen atom can be avoided due to the ring strain of molecular structure of functional group. Therefore, high activity can be achieved if a is between 5 to 10. This result is also presented in the *Journal of Organometallic Chemistry* 552, 313 (1998) by the authors of this invention.

The metallocene compounds in this invention may be synthesized by a conventional method. That is, a substituted cyclopentadienyl ligand with a suitable functional group is prepared by an organic reaction and then reacted with a zirconium chloride. However, the synthesis of a substituted cyclopentadienyl ligand with a desired functional group is usually difficult. Especially, if Y is a halogen atom, the anionic cyclopentadienyl group reacts with the halogen on the Si atom instead of that on the metal during the metallation step and leads to unwanted products.

The metallocene compound in this invention can be prepared by a novel method as shown in Reaction Formula 6 below. The reaction of metal halide with cyclopentadienide anion substituted with alkylhydroxy group yields metallocene compound in which the both the cyclopentadiene group and alkoxide group of the cyclopentadienyl ligand are coordinated to the same metal, or dimetallic or multimetallic compounds in which the transition metals are connected via the cyclopentadiene group and alkoxide group of the cyclopentadienyl ligand. Reaction of this intermediate metallocene compound with $R_bY_cSiX$ produces the desired product. In this formula, X stands for a halogen radical. In case Y is a halogen radical, this halogen radical can be transformed to alkoxy, aryloxy, or amide radicals.

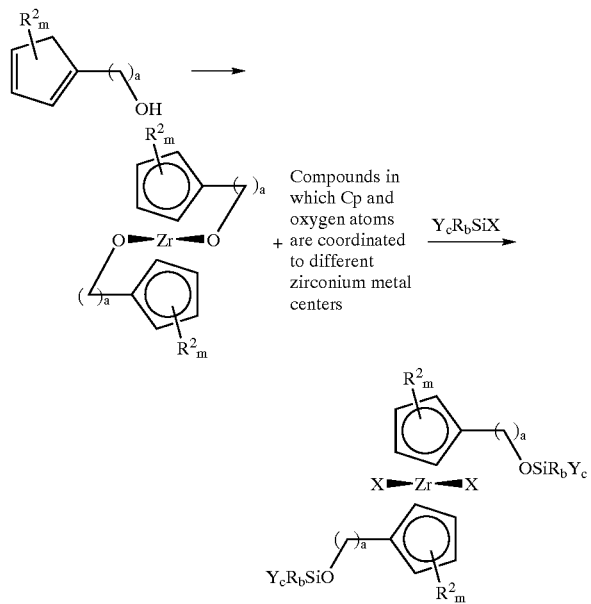

Examples of compound described in the above Chemical Formula 4 include methylaluminoxane, ethylaluminoxane, isobutylaluminoxane, butylaluminoxane, etc.

Examples of alkyl metal compounds described in the above Chemical Formula 5 include triethylaluminum, triethylaluminum, triisobutylaluminum, tripropylaluminum, tributylaluminum, dimethylchloroaluminum, dimethylisobutylaluminum, ethyldimethylaluminum, diethylchloroaluminum, triisopropylaluminum, tri-s-butylaluminum, tricyclopentylaluminum, tripentylaluminum, triisopentylaluminum, trihexylaluminum, methyldiethylaluminum, ethyldimethylaluminum, triphenylaluminum, tri-p-tolylaluminum, dimethylaluminummethoxide, dimethylaluminumethoxide, etc.

Examples of compound in Chemical Formula 6 include triethylammoniumtetraphenylborate, tributylammoniumtetraphenylborate, trimethylammoniumtetraphenylborate, tripropylammoniumtetraphenylborate, trimethylammoniumtetrakis(p-tolyl)borate, triethylammoniumtetrakis(o,p-dimethylphenyl)borate, trimethylammoniumtetrakis(o,p-dimethylphenyl)borate, tributylammoniumtetrakis(p-trifluoromethylphenyl)borate, trimethylammoniumtetrakis(p-trifluoromethylphenyl)borate, tributylammoniumtetrakispentafluorophenylborate, N,N-diethylaniliniumtetraphenylborate, N,N-dimethylaniliniumtetraphenylborate, N,N-diethylaniliniumtetrakispentafluorophenylborate, diethylammoniumtetrakispentafluorophenylborate, triphenylphosphoniumtetraphenylborate, trimethylphosphoniumtetraphenylborate, triethylammoniumtetraphenylaluminate, tributylammoniumtetraphenylaluminate, trimethylammoniumtetraphenylaluminate, tripropylammoniumtetraphenylaluminate, trimethylammoniumtetrakis(p-tolyl)aluminate, triethylammoniumtetrakis(o,p-dimethylphenyl)aluminate, tributylammoniumtetrakis(p-trifluoromethylphenyl)aluminate, trimethylammoniumtetrakis(p-trifluoromethylphenyl)aluminate, tributylammoniumtetrakispentafluorophenylaluminate, N,N-diethylaniliniumtetraphenylaluminate, N,N-dimethylaniliniumtetraphenylaluminate, N,N-diethylaniliniumtetrakispentafluoropenylaluminate, diethylammoniumtetrakispentafluorophenylaluminate, triphenylphosphoniumtetraphenylaluminate, trimethylphosphoniumtetraphenylaluminate, Triethylammoniumtetraphenylborate, tributylammoniumtetraphenylborate, trimethylammoniumtetraphanylborate, tripropylammoniumtetraphenylborate, trimethylammoniumtetrakis(p-tolyl)borate, tripropylammoniumtetrakis(p-tolyl)borate, triethylammoniumtetrakis(o,p-dimethylphenyl)borate, trimethylammoniumtetrakis(o,p-dimethylphenyl)borate, tributylammoniumtetrakis(p-trifluoromethylphenyl)borate, trimethylammoniumtetrakis(p-trifluoromethylphenyl)borate, tributylammoniumtetrakispentafluorophenylborate, N,N-diethylaniliniumtetraphenylborate, N,N-diethylaniliniumtetraphenylborate, N,N-diethylaniliniumtetrakispentafluorophenylborate, diethylammoniumtetrkispentafluorohenylborate, triphenylphsphoniumtetraphenylborate, triphenylcarboniumtetraphenylborate, triphenylcarboniumtetraphenylaluminate, triphenylcarboniumtetrakis(p-trifluoromethylphenyl)borate, triphenylcarboniumtetrakispentafluorophenylborate, etc.

The metallocene in this invention can be used to make supported metallocene catalyst by supporting on a suitable porous inorganic support. Examples of the appropriate supports are silica, alumina, aluminum silicate or mixtures of them. These supports usually contain oxides, carbonates, sulfates, or nitrates salts such as $Na_2O$, $K_2CO_3$, $BaSO_4$, or $Mg(NO_3)_2$. The support can be used after elimination of the physisorbed or hydrogen-bonded water. Also, the desired amount of the surface hydroxyl group can be controlled by changing dehydration temperature. The anchoring can also be accomplished by utilizing the support which is dried above 500° C. and contains highly reactive surface siloxane groups.

This invention provides a supported metallocene catalyst by reacting the metallocene compounds with a support. Solvents for the supporting process can be aliphatic hydrocarbon solvents such as hexane or heptane, aromatic hydrocarbon solvents such as toluene or benzene, chlorinated hydrocarbon solvents such as dichloromethane, ethers such as diethyl ether or THF (tetrahydrofuran), or other common organic solvents such as acetone or ethylacetate. However, hexane, heptane, toluene, or dichloromethane are recommended. Furthermore, the anchoring can be achieved without solvent. This reaction can be performed at the temperature range of −30° C. to 300° C., but the temperature range of RT to 100° C. is desirable.

In combination of co-catalyst of the Chemical Formula 3, 4, 5 or any mixtures of them, the supported metallocene catalyst prepared in this method can be used for the olefin polymerization process.

In the olefin polymerization process utilizing the metallocene or supported metallocene catalyst and the co-catalyst described above, solvent can be selected from aliphatic hydrocarbon solvents with 3 to 12 carbons such as propane, butane, isobutane, pentane, hexane, heptane, octane, nonane, decane, or isomers of them, aromatic hydrocarbon solvents such as toluene or benzene, chlorinated hydrocarbon solvents such as dichloromethane or chlorobenzene, or any mixtures of them.

It is also possible to perform the olefin polymerization process in a gas phase or in a bulk phase with the metallocene catalyst and the co-catalyst described above without employing any solvent.

Examples of olefin based monomer, which can be polymerized using the catalyst or supported catalyst with the co-catalyst described above include ethylene, α-olefin, cyclic olefin, diene olefinc monomers having more than two double bonds, triene monomers, polyene monomers, etc. Examples of the monomers described above include ethylene, propylene, 1-butene, 2-butene, 1-pentene, 2-pentene, 4-methyl-1-pentene, 1-hexene, 1-heptene, 1-octene, 1-nonene, 1-decene, 1-undecene, 1-dodecene, 1-tetradecene, 1-hexandecene, 1-icocene, cyclopentadiene, norbornene, norbornadiene, ethylidenenorbornene, vinylnorbornene, dicyclopentadiene, 1,4-butadiene, 1,5-pentadiene, 1,6-hexadiene, styrene, α-methylstyrene, divinylbenzene, 3-chloromethylstyrene, etc. Co-polymerization can be accomplished by employing more than one of these monomers. Polymerization is performed at temperature ranging from −25° C. to 500° C. and at the pressure ranging from 10 to 500 bar. It is preferable to add co-catalyst is an amount that is 1 to 30,000 times the metallocene mole content. In the present invention, the contact order and input order of catalyst, co-catalyst, solvent, and monomer are not particularly restricted. That is, polymerization is done by putting the above described supported catalyst and co-catalyst into suspension solvents simultaneously, or main polymerization can be performed after either the activation reaction or pre-polymerization. The main polymerization can be carried out in a suitable suspension solution by introucing monomers. It may also be done in a gas phase or in a bulk phase without solvent. Prepolymerized catalyst is prepared from the supported catalyst and the co-catalyst under the suitable olefin polymerization conditions. It is then separated from the solvent either by a filtration or decantation. The activated catalyst can be obtained by the same method of prepolymerization reaction without olefin monomer. Treatment of the supported catalyst with organic aluminum compound before the polymerization process can reduce the amount of methylaluminoxane (MAO) required.

Although the present invention is illustrated by the following EXAMPLES in detail, the scope of the present invention is not limited by these EXAMPLES.

EXAMPLES

The manufacturing of metallocene catalysts and supported metallocene catalysts in which the metallocene catalysts are supported onto a support are mainly described in following EXAMPLES, wherein it can be shown that the other above described metallocene catalysts and supported metallocene catalysts can also be manufactured in the same method only by changing the selected raw materials. The catalyst thus prepared can be used for the polymerization of monomers such as ethylene either by not supporting them or by supporting them on supports on a support or in the absence of support.

Organic reagents and solvents for the catalyst synthesis and polymerization process were purchased from Aldrich and Merck and then purified by standard methods. High purity ethylene gas from Applied Gas Technology was polymerized after passing through moisture and oxygen scavenging filter. Reproducibility was maintained by performing all stages of catalyst synthesis, supporting and polymerization under inert gas atmosphere. The catalysts were analyzed by a Nuclear Magnetic Resonance (NMR) spectroscopy employing either a 300 MHz Bruker or a 500 MHz Jeol instruments. The NMR samples were prepared in a $CDCl_3$ solution. The amount of catalysts supported was determined by measuring Zr content using the Inductively Coupled Plasma (ICP-AES Integra XMP, GBC) spectroscopic method.

Example 1 a) The synthesis of $[ClMe_2SiO—(CH_2)_6—C_5H_4]_2ZrCl_2$

To a flask containing 9.14 g of 1,6-hexanediol and 15.7 g of p-toluenesulfonyl chloride, 50 mL of pyridine was added. The solution was kept in a refrigerator for a day. The solution was then treated with 500 mL of 2 N HCl and the product was extracted with 100 mL of diethyl ether. The ether solution was dried with anhydrous $MgSO_4$, filtered and then ether was removed from the filtrate under reduced pressure. The product which was tosylated on one of the hydroxyl group was purified by passing through a silica gel column with diethyl ether (Yield: 9.00 g, 40%).

8.12 g of the tosylated product is dissolved in 100 mL of anhydrous THF. This solution was cooled down to 0° C. and 45 mL of 2N THF solution of NaCp was added to the cold solution. This solution was stirred for about 3 hours, and mixed with 400 mL of water and 100 mL of hexane. The organic layer was extracted and refined by passing through a silica gel column with hexane and diethyl ether (v/v=1:1) to give 4.07 g of product, (6-hydroxy)hexylcyclopentadiene (Yield: 82%).

0.98 g of this compound was dissolved in 40 mL of THF, cooled down to −78° C., and 2 equivalent of n-BuLi was added to the cold solution. Temperature was slowly raised to RT and the solution was stirred another 2 hours. To this solution, 0.5 equivalent of $ZrCl_4.2THF$ was added and it was stirred for overnight at 50° C. On the next day, 10 equivalents of dichlorodimethylsilane was added to the solution, which was then stirred for 4 hours at RT. All volatimes were removed under vacuum and the product was extracted with hexane (Yield: 46%).

Spectroscopic analysis by the NMR method is as follows:
$^1H$ NMR (δ, 300 MHz, $CDCl_3$): 6.29 (t, 2H), 6.20 (t, 2H), 3.72 (t, 2H), 2.60 (t, 2H), 1.6~1.2 (m, 8H), 0.45 (s, 6H).

b) Preparation of supported catalyst

To 70 mL of toluene solution containing 1.32 mmol of the catalyst made above, 15.27 g of the silica, Grace Davison XPO 2412, was added. The solution was bubbled with $N_2$ at 70° C. to remove evolved HCl. The HCl evolution was stopped in about 5 hours, which was confirmed by a litmus paper. The solution was left undisturbed for 10 hours. Toluene was decanted from the solution and the supported catalyst was dried under vacuum.

c) Polymerization

In a dry box 100 mg of the supported catalyst was weighed and transferred to a glass reactor. The glass reactor was sealed, removed from the dry box and filled with 100 mL of refined hexane and 0.67 mL of heptane solution of aluminoxane (2.0 mmole, DMAO, 10.5% Al, Albemarle). The reactor was pressurized with 40 psig ethylene atmosphere, and the solution was stirred at RT for 40 minutes. The organic solution was then removed from the precipitates and 250 mL of hexane solution containing 0.25 mmol of triisobutylaluminum was transferred to the reactor under an inert gas atmosphere. Polymerization was performed at 80° C. for 70 min. under 60 psig atmosphere of ethylene. Hexane was decanted from the reactor, and the obtained polymer was dried at 80° C. to give 14.8 g of product. The polymerization activity was determined to be 391 Kg PE/mole of Zr hr atm. Bulk density of the polymer was 0.35 g/mL and no foulng in the reactor was observed.

Example 2 a) The synthesis of $[HMe_2SiO—(CH_2)_6—C_5H_4]_2ZrCl_2$

To an ice-cooled 278 mL of 2N THF solution of NaCp, 30 g of chlorohexanol was added slowly. The reaction solution was warmed to RT slowly and stirred overnight. The solution was then mixed with 200 mL of distilled water and 100 mL of diethyl ether. The organic layer was extracted and dried with anhydrous $MgSO_4$. $MgSO_4$ was separated by a filtration and the diethyl ether was removed from the filtrate under reduced pressure. The product, (6-hydroxy) hexylcyclopentadiene, was distilled at 100° C. at 0.2 mbar to give 17.7 g (Yield: 40%).

To 100 mL of THF of the 17.56 g of the product at −30° C., 85 mL of n-BuLi was added slowly. The solution was then warmed to RT slowly and stirred another 2 hours. To this solution 0.5 equivalent of $ZrCl_4.2THF$ was added and stirred overnight at 50° C. On the next day, 1.5 equivalents of chlorodimethylsilane was added to the solution, which was then stirred for 3 hours at RT. All volatiles were removed under vacuum and the product was extracted with hexane (Yield: 52%).

Spectroscopic analysis by the NMR method is as follows:
$^1$H NMR ($\delta$, 500 MHz, $CDCl_3$): 6.27 (t, 2H), 6.18 (t, 2H), 4.59(t, 1H), 2.60 (t, 2H), 2.61 (t, 2H), 1.5~1.3 (m, 8H), 0.19 (s, 6H).

b) Preparation of supported catalyst

Silica support, Grace Davison (XPO 2412), was dried at 800° C. under vacuum for 15 hours. To 40 mL of hexane solution containing 100 mg of the catalyst made above, 1 g of the dried silica was added. The solution was left for 4 hours at 85° C. Hexane was decanted from the solution and the supported catalyst was dried under vacuum. 0.93 wt % of Zr content on the silica was determined by the Inductively Coupled Plasma (ICP) spectroscopic method.

c) Polymerization

In a dry box 100 mg of the supported catalyst was weighed and transferred to a glass reactor. The glass reactor was sealed, removed from the dry box and filled with 100 mL of refined hexane and 1.06 mL of heptane solution of aluminoxane (2.0 mmole, MMAO-3A, 7.2% Al, Akzo). The reactor was fed with ethylene at the rate of 50 cc/min for 15 minutes, and the solution was stirred at 40° C. for 40 minutes. The organic solution was then removed from the reactor and the precipitates was transferred to a Büchi reactor containing 1L of hexane solution of trimethylaluminum, 0.6 mmole/L, under an inert gas atmosphere. Polymerization was performed at 80° C. for 60 minutes under 9 bar ethylene atmosphere. Hexane was decanted from the reactor, and the obtained polymer was dried at 80° C. to give 109 g of product. The polymerization activity was determined to be 813 Kg PE/mole of Zr hr atm. No foulng was observed in the reactor.

Example 3 a) The synthesis of $[(MeO)Me_2SiO—(CH_2)_6—C_5H_4]_2ZrCl_2$

To 10 mL of anhydrous trimethylorthoformate, 1.37 g of the catalyst shown in Example 1, $[ClMe_2SiO—(CH_2)_6—C_5H_4]_2ZrCl_2$ and 2 mg of $AlCl_3$ were added under inert gas atmosphere. The solution was stirred overnight. All volatiles were removed under vacuum from the reaction mixture and the product was extracted with hexane. Hexane was taken off under vacuum to give 70% yield of the product.

Spectroscopic analysis by the NMR method is as follows:
$^1$H NMR ($\delta$, 500 MHz, $CDCl_3$): 6.27 (s, 2H), 6.18 (s, 2H), 3.64 (m, 2H), 3.48 (s, 3H), 2.61 (t, 2H), 1.53~1.33 (m, 8H), 0.11 (s, 6H).

b) Preparation of supported catalyst

Silica support, Grace Davison C 948, was dried at 800° C. under vacuum for 15 hours. To 40 mL of toluene solution containing 100 mg of the catalyst made above, 1 g of the dried silica was added. The solution was left for 24 hours at 85° C. Toluene was decanted from the solution. Weakly bound or physisorbed complexes on the silica surface were extracted by a soxhlet method. The supported catalyst was then dried under vacuum. 0.8 wt % of Zr content on the silica was determined by the Inductively Coupled Plasma (ICP) spectroscopic method.

b) Polymerization

Polymerization with 100 mg of the supported catalyst as Example 2 yielded 65 g of polymers. The polymerization activity was determined to be 533 Kg PE/mole of Zr hr atm. No fouling was observed in the reactor.

Comparative Example

The following test was undertaken in order to show that the catalysts of the present invention were better supported on a support than catalysts disclosed in European Patent Laid-Open No. 839,836 A1. In this test, activated supernatant solution which is decanted from the activated suspension of supported catalyst in used for a polymerization, and the catalyst from this invention is compared to $[Me_3SiO—(CH_2)_6—C_5H_4]_2ZrCl_2$ disclosed in the above European Patent.

100 mg of $[Me_3SiO—(CH_2)_6—C_5H_4]_2ZrCl_2$ was supported on 1 g of dry silica as Example 2-b. Zirconium content of 1.0% on a silica surface was determined by the ICP method. 200 mg of supported catalyst was placed in a glass reactor under inert gas atmosphere. 200 mL of hexane solution of MMAO-3A, 4 mmole, was transferred to this solution and the catalyst was activated at 40° C. for an hour. 150 mL of hexane solution containing MMAO-3A except for the supported catalyst was transferred from this activated solution to a different glass reactor. Polymerization with this solution containing leached catalyst was performed at 80° C. under 60 psig ethylene atmosphere.

Same experiment was performed with 200 mg of the supported catalyst prepared as in Example 2-b under the same condition to compare the amount of the leached catalyst.

Polyethylene products from the leached catalysts are as follows.

[HMe$_2$SiO—(CH$_2$)$_6$—C$_5$H$_4$]$_2$ZrCl$_2$: 1.08 g
[Me$_3$SiO—(CH$_2$)$_6$—C$_5$H$_4$]$_2$ZrCl$_2$: 1.77 g

The polyethylenes produced in this comparative example are polymerized by unsupported catalysts or physisorbed catalysts which are leached out of a support upon activation by a co-catalyst. This results indicates that catalyst in this invention is supported strongly on a support compared to that disclosed in the above European patent.

The metallocene compounds in this invention has superior characteristics in the preparation of supported catalyst due to the high reactivity with the support and minimal side reactions during the anchoring process. In addition, the olefin polymerization process employing the supported catalyst in this invention proceeds without fouling in the reactor, and the morphology and bulk density of the polymer produced are better than that produced by the conventional method.

Although preferred embodiments of the present invention have been described in detail hereinabove, it should be clearly understood that many variations and/or modifications of the basic inventive concepts herein taught which may appear to those skilled in the present art will still fall within the spirit and scope of the present invention, as defined in the appended claims.

What is claimed is:

1. A metallocene compound comprising one or more compounds represented by the following Chemical Formulae 1 or 2 in which at least one of the hydrogen radicals of R$^2$, R$^3$ or B is substituted by a radical selected from the group represented by the Chemical Formula 3:

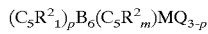  [Chemical Formula 1]

[Chemical Formula 2]

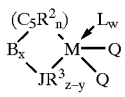

(wherein M is a transition metal of Group 4;
(C$_5$R$^2_1$), (C$_5$R$^2_m$) and (C$_5$R$_n^2$) are a cyclopentadienyl ligand, a substituted cyclopentadienyl ligand, a substituted cyclopentadienyl ligand in which two adjacent carbon atoms of a C$_5$ are joined together to form one or more C$_4$–C$_{16}$ rings by a hydrocarbyl radical, in which each R$^2$, which can be the same as or different from other R$^2$, is a hydrogen radical, or an alkyl, cycloalkyl, aryl, alkenyl, alkylaryl, arylalkyl, or arylalkenyl radical having from 1 to 40 carbon atoms, or a metalloid of Group 14 substituted with hydrocarbyl radical;

B is an alkylene carbon chain, arylene carbon chain, alkenylene carbon chain, dialkyl germanium, dialkyl silicon, alkyl phospine or alkyl amine radical substituting on and bridging two cyclopentadienyl ligands, or a cyclopentadienyl ligand and JR$^3_{z-y}$ ligands by a covalent bond;

R$^3$ is a hydrogen radical, or an alkyl, alkenyl, aryl, alkylaryl, or arylalkyl radical having from 1 to 40 carbon atoms;

J is an element of Group 15 or 16;

each Q, which can be the same as or different from other Q, is a halogen radical, an alkyl, alkenyl, aryl, alkylaryl, or arylalkyl radical having from 1 to 20 carbon atoms, or an alkylidene radical having from 1 to 20 carbon atoms;

L is a Lewis base;

s is 0 or 1, p is 0, 1, or 2; (provided that p is 0 then s is 0; when s is 1 then l and m is 4; and when s is 0 then l and m is 5), and z is a valence number of J;

provided that J is an atom of Group 15, then z is 3; and when J is an atom of Group 16, then z is 2;

x is 0 or 1;

provided that x is 0, then n is 5, y is 1, and w is greater than 0; when x is 1, then n is 4, y is 2, and w is 0),

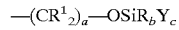  [Chemical Formula 3]

(wherein each R$^1$, which can be the same as or different from other R$^1$, is a hydrogen radical, or an alkyl, cycloalkyl, aryl, alkenyl, alkylaryl, arylalkyl, or arylalkenyl radical having from 1 to 40 carbon atoms, each R, which can be the same as or different from other R, is an alkyl, cycloalkyl, aryl, alkenyl, alkylaryl, arylalkyl, or arylalkenyl radical having from 1 to 40 carbon atoms, each Y, which can be the same as or different from other Y, is a hydrogen, halogen, alkoxy, aryloxy, or amide radical, a is an integral number from 1 to 40, c is 1, 2, or 3, and the sum of b and c is 3).

2. A metallocene compound in accordance with claim 1, wherein p is 1.

3. A method for polymerizing one or more olefins in which the polymerization is performed in the presence of the catalyst system comprising:

a) a metallocene compound comprising one or more compounds by the following Chemical Formulae 1 or 2 in which at least one of the hydrogen radicals of R$^2$, R$^3$ is substituted by a radical selected from the group represented by the Chemical Formula 3; and one or more of co-catalysts selected from the compounds

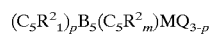  [Chemical Formula 1]

[Chemical Formula 2]

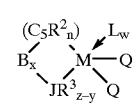

(wherein M is a transition metal of Group 4;
(C$_5$R$^2_1$), (C$_5$R$^2_m$) and (C$_5$R$_n^2$) are a cyclopentadienyl ligand, a substituted cyclopentadienyl ligand, a substituted cyclopentadienyl ligand in which two adjacent carbon atoms of a C$_5$ are joined together to form one or more C$_4$–C$_{16}$ rings by a hydrocarbyl radical, in which each R$^2$, which can be the same as or different from other R$^2$, is a hydrogen radical, or an alkyl, cycloalkyl, aryl, alkenyl, alkylaryl, arylalkyl, or arylalkenyl radical having from 1 to 40 carbon atoms, or a metalloid of Group 14 substituted with hydrocarbyl radical;

B is an alkylene carbon chain, arylene carbon chain, alkenylene carbon chain, dialkyl germanium, dialkyl silicon, alkyl phospine or alkyl amine radical substituting on and bridging two cyclopentadienyl ligands, or a cyclopentadienyl ligand and JR$^3_{z-y}$ ligands by a covalent bond;

R$^3$ is a hydrogen radical, or an alkyl, alkenyl, aryl, alkylaryl, or arylalkyl radical having from 1 to 40 carbon atoms;

J is an element of Group 15 or 16;

each Q, which can be the same as or different from other Q, is a halogen radical, an alkyl, alkenyl, aryl, alkylaryl, or arylalkyl radical having from 1 to 20 carbon atoms, or an alkylidene radical having from 1 to 20 carbon atoms;

L is a Lewis base;

s is 0 or 1, p is 0, 1, or 2; (provided that p is 0 then s is 0; when s is 1 then l and m is 4; and when s is 0 then l and m is 5), and z is a valence number of J;

provided that J is an atom of Group 15, then z is 3; and when J is an atom of Group 16, then z is 2;

x is 0 or 1;

provided that x is 0, then n is 5, y is 1, and w is greater than 0; when x is 1, then n is 4, y is 2, and w is 0),

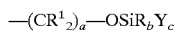  [Chemical Formula 3]

(wherein each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms, each R, which can be the same as or different from other R, is an alkyl, cycloalkyl, aryl, alkenyl, alkylaryl, arylalkyl, or arylalkenyl radical having from 1 to 40 carbon atoms, each Y, which can be the same as or different from other Y, is a hydrogen, halogen, alkoxy, aryloxy, or amide radical, a is an integral number from 1 to 40, c is 1, 2, or 3, and the sum of b and c is 3),

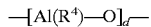  [Chemical Formula 4]

(wherein each $R^4$, which can be the same as or different from other $R^4$, is a halogen, or a hydrocarbyl or a halogen substituted hydrocarbyl radical having from 1 to 40 carbon atoms, and d is an integral number greater than 2),

  [Chemical Formula 5]

(wherein each $R^5$, which can be the same as or different from other $R^5$, is a halogen, or a hydrocarbyl or a halogen substituted hydrocarbyl radical having from 1 to 40 carbon atoms), and

  [Chemical Formula 6]

(wherein, $[L]^+$ is a cation composed of inorganic or organic group, N is an element of Group 13, each E, which can be the same as or different from other E, is an aryl radical having from 6 to 40 carbon atoms, where more than one hydrogen radical of the aryl group is substituted with halogen radical, hydrocarbyl radical containing 1 to 40 carbons, alkoxy radical, phenoxy radical, or hydrocarbyl radical having from 1 to 40 carbon atoms containing nitrogen, phosphorus, sulfur or oxygen atom).

4. A supported metallocene catalyst prepared by supporting
   a) a metallocene compound comprising one or more compounds represented by the following Chemical Formulae 1 or 2 in which at least one of the hydrogen radicals of $R^2$, $R^3$ or B is substituted by a radical selected from the group represented by the Chemical Formula 3; and
   b) inorganic support

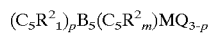  [Chemical Formula 1]

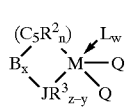  [Chemical Formula 2]

(wherein M is a transition metal of Group 4;

$(C_5R^2_1)$, $(C_5R^2_m)$ and $(C_5R_n^2)$ are a cyclopentadienyl ligand, a substituted cyclopentadienyl ligand, a substituted cyclopentadienyl ligand in which two adjacent carbon atoms of a $C_5$ are joined together to form one or more $C_4$–$C_{16}$ rings by a hydrocarbyl radical, in which each $R^2$, which can be the same as or different from other $R^2$, is a hydrogen radical, or an alkyl, cycloalkyl, aryl, alkenyl, alkylaryl, arylalkyl, or arylalkenyl radical having from 1 to 40 carbon atoms, or a metalloid of Group 14 substituted with hydrocarbyl radical;

B is an alkylene carbon chain, arylene carbon chain, alkenylene carbon chain, dialkyl germanium, dialkyl silicon, alkyl phospine or alkyl amine radical substituting on and bridging two cyclopentadienyl ligands, or a cyclopentadienyl ligand and $JR^3_{z-y}$ ligands by a covalent bond;

$R^3$ is a hydrogen radical, or an alkyl, alkenyl, aryl, alkylaryl, or arylalkyl radical having from 1 to 40 carbon atoms;

J is an element of Group 15 or 16;

each Q, which can be the same as or different from other Q, is a halogen radical, an alkyl, alkenyl, aryl, alkylaryl, or arylalkyl radical having from 1 to 20 carbon atoms, or an alkylidene radical having from 1 to 20 carbon atoms;

L is a Lewis base;

s is 0 or 1, p is 0, 1, or 2; (provided that p is 0 then s is 0; when s is 1 then l and m is 4; and when s is 0 then l and m is 5), and z is a valence number of J;

provided that J is an atom of Group 15, then z is 3; and when J is an atom of Group 16, then z is 2;

x is 0 or 1;

provided that x is 0, then n is 5, y is 1, and w is greater than 0; when x is 1, then n is 4, y is 2, and w is 0), and

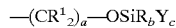  [Chemical Formula 3]

(wherein each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms, each R, which can be the same as or different from other R, is an alkyl, cycloalkyl, aryl, alkenyl, alkylaryl, arylalkyl, or arylalkenyl radical having from 1 to 40 carbon atoms, each Y, which can be the same as or different from other Y, is a hydrogen, halogen, alkoxy, aryloxy, or amide radical, a is an integral number from 1 to 40, c is 1, 2, or 3, and the sum of b and c is 3).

5. A supported metallocene catalyst in accordance with claim 4, wherein the inorganic support of b) is one or more inorganic supports selected from a group comprising silica, alumina, or aluminum silicate.

6. A supported metallocene catalyst in accordance with claim 4, wherein the inorganic support of b) is silica the surface of which contains hydroxyl groups or reactive siloxane groups by drying at the temperature above 500° C.

7. A polymerization method for polymerizing one or more olefins employing a catalyst system comprising:
   a) a supported metallocene catalyst prepared by supporting
      i) a metallocene compound comprising one or more compounds represented by the following Chemical Formulae 1 or 2 in which at least one of the hydrogen radicals of $R^2$, $R^3$ or B is substituted by a radical selected from the group represented by Chemical Formula 3; and
      ii) inorganic support; and
   b) one or more of co-catalysts selected from the compounds represented by the Chemical Formulae 4, 5 or 6 shown below:

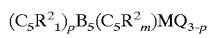     [Chemical Formula 1]

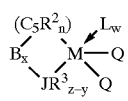     [Chemical Formula 2]

(wherein M is a transition metal of Group 4;

$(C_5R^2_1)$, $(C_5R^2_m)$ and $(C_5R^2_n)$ are a cyclopentadienyl ligand, a substituted cyclopentadienyl ligand, a substituted cyclopentadienyl ligand in which two adjacent carbon atoms of a $C_5$ are joined together to form one or more $C_4$–$C_{16}$ rings by a hydrocarbyl radical, in which each $R^2$, which can be the same as or different from other $R^2$, is a hydrogen radical, or an alkyl, cycloalkyl, aryl, alkenyl, alkylaryl, arylalkyl, or arylalkenyl radical having from 1 to 40 carbon atoms, or a metalloid of Group 14 substituted with hydrocarbyl radical;

B is an alkylene carbon chain, arylene carbon chain, alkenylene carbon chain, dialkyl germanium, dialkyl silicon, alkyl phospine or alkyl amine radical substituting on and bridging two cyclopentadienyl ligands, or a cyclopentadienyl ligand and $JR^3_{z-y}$ ligands by a covalent bond;

$R^3$ is a hydrogen radical, or an alkyl, alkenyl, aryl, alkylaryl, or arylalkyl radical having from 1 to 40 carbon atoms;

J is an element of Group 15 or 16;

each Q, which can be the same as or different from other Q, is a halogen radical, an alkyl, alkenyl, aryl, alkylaryl, or arylalkyl radical having from 1 to 20 carbon atoms, or an alkylidene radical having from 1 to 20 carbon atoms;

L is a Lewis base;

s is 0 or 1, p is 0, 1, or 2; (provided that p is 0 then s is 0; when s is 1 then l and m is 4; and when s is 0 then l and m is 5), and z is a valence number of J;

provided that J is an atom of Group 15, then z is 3; and when J is an atom of Group 16, then z is 2;

x is 0 or 1;

provided that x is 0, then n is 5, y is 1, and w is greater than 0; when x is 1, then n is 4, y is 2, and w is 0),

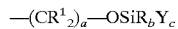     [Chemical Formula 3]

(wherein each $R^1$, which can be the same as or different from other $R^1$, is a hydrogen radical, or an alkyl, cycloalkyl, aryl, alkenyl, alkylaryl, arylalkyl, or arylalkenyl radical having from 1 to 40 carbon atoms, each R, which can be the same as or different from other R, is an alkyl, cycloalkyl, aryl, alkenyl, alkylaryl, arylalkyl, or arylalkenyl radical having from 1 to 40 carbon atoms, each Y, which can be the same as or different from other Y, is a hydrogen, halogen, alkoxy, aryloxy, or amide radical, a is an integral number from 1 to 40, c is 1, 2, or 3, and the sum of b and c is 3),

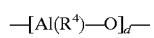     [Chemical Formula 4]

(wherein each $R^4$, which can be the same as or different from other $R^4$, is a halogen, or a hydrocarbyl or a halogen substituted hydrocarbyl radical having from 1 to 40 carbon atoms, and d is an integral number greater than 2),

     [Chemical Formula 5]

(wherein each $R^5$, which can be the same as or different from other $R^5$, is a halogen, or a hydrocarbyl or a halogen substituted hydrocarbyl radical having from 1 to 40 carbon atoms), and

     [Chemical Formula 6]

(wherein, $[L]^+$ is a cation composed of inorganic or organic group, N is an element of Group 13, each E, which can be the same as or different from other E, is an aryl radical having from 6 to 40 carbon atoms, where more than one hydrogen radical of the aryl group is substituted with halogen radical, hydrocarbyl radical containing 1 to 40 carbons, alkoxy radical, phenoxy radical, or hydrocarbyl radical having from 1 to 40 carbon atoms containing nitrogen, phosphorus, sulfur or oxygen atom).

8. A polymerization method in accordance with claim 7, wherein inorganic support of a) ii) is one or more organic supports selected from a group comprising silica, alumina, or aluminum silicate.

9. A polymerization method in accordance with claim 7, wherein the support of a) ii) is silica dried at the temperature above 500° C.

10. A polymerization method in accordance with claim 7, wherein the co-catalyst of b) is a mixture of a compound represented by the Chemical Formula 4 and a compound represented by the Chemical Formula 5.

11. A polymerization method is accordance with claim 7, wherein the olefin is ethylene or α-olefin.

12. A polymerization method in accordance with claim 7, wherein the polymerization is carried out in a slurry or a gas phase.

* * * * *